(12) United States Patent
Purola

(10) Patent No.: US 8,389,776 B2
(45) Date of Patent: Mar. 5, 2013

(54) TREATMENT OF PHENOL

(75) Inventor: Veli-Matti Purola, Hamari (FI)

(73) Assignee: Borealis Technology Oy, Ponvoo (FI)

( * ) Notice: Subject to any disclaimer, the term of this patent is extended or adjusted under 35 U.S.C. 154(b) by 313 days.

(21) Appl. No.: 12/808,369

(22) PCT Filed: Dec. 22, 2008

(86) PCT No.: PCT/EP2008/011007
§ 371 (c)(1),
(2), (4) Date: Jun. 21, 2010

(87) PCT Pub. No.: WO2009/080340

PCT Pub. Date: Jul. 2, 2009

(65) Prior Publication Data

US 2010/0280285 A1    Nov. 4, 2010

(30) Foreign Application Priority Data

Dec. 20, 2007 (EP) .................................... 07150229

(51) Int. Cl.
*C07C 37/80* (2006.01)
(52) U.S. Cl. .................. 568/754; 568/749; 568/758
(58) Field of Classification Search .................. 568/754
See application file for complete search history.

(56) References Cited

U.S. PATENT DOCUMENTS

| 3,029,294 A | | 4/1962 | Keeble | |
|---|---|---|---|---|
| 5,456,806 A | * | 10/1995 | Lorenzoni et al. | ............... 203/62 |
| 6,657,087 B2 | * | 12/2003 | Weber et al. | .................. 568/385 |

FOREIGN PATENT DOCUMENTS

| EP | 0571042 | 11/1993 |
|---|---|---|
| GB | 920864 | 3/1953 |
| GB | 1231991 | 5/1971 |
| WO | 2009/080339 A2 | 7/2009 |

OTHER PUBLICATIONS

Database CAPLUS on STN, Acc. No. 1982:37268, Bahr et al., DD 150351 (Aug. 26, 1981) (abstract).*

* cited by examiner

*Primary Examiner* — Brian J Davis
(74) *Attorney, Agent, or Firm* — Sutherland Asbill & Brennan LLP

(57) ABSTRACT

A process for the removal of by-products from a phenolic mixture, which process may include the following steps: subjecting a phenolic mixture to extractive distillation to produce an initial phenolic mixture, contacting the initial phenolic mixture containing phenol and one or more by products with a catalyst to produce a first purified phenol product mixture, and distilling the first purified phenol product mixture to produce a second purified phenol product mixture; wherein the extractive distillation is carried out in two columns, a higher pressure column and a lower pressure column.

28 Claims, 1 Drawing Sheet

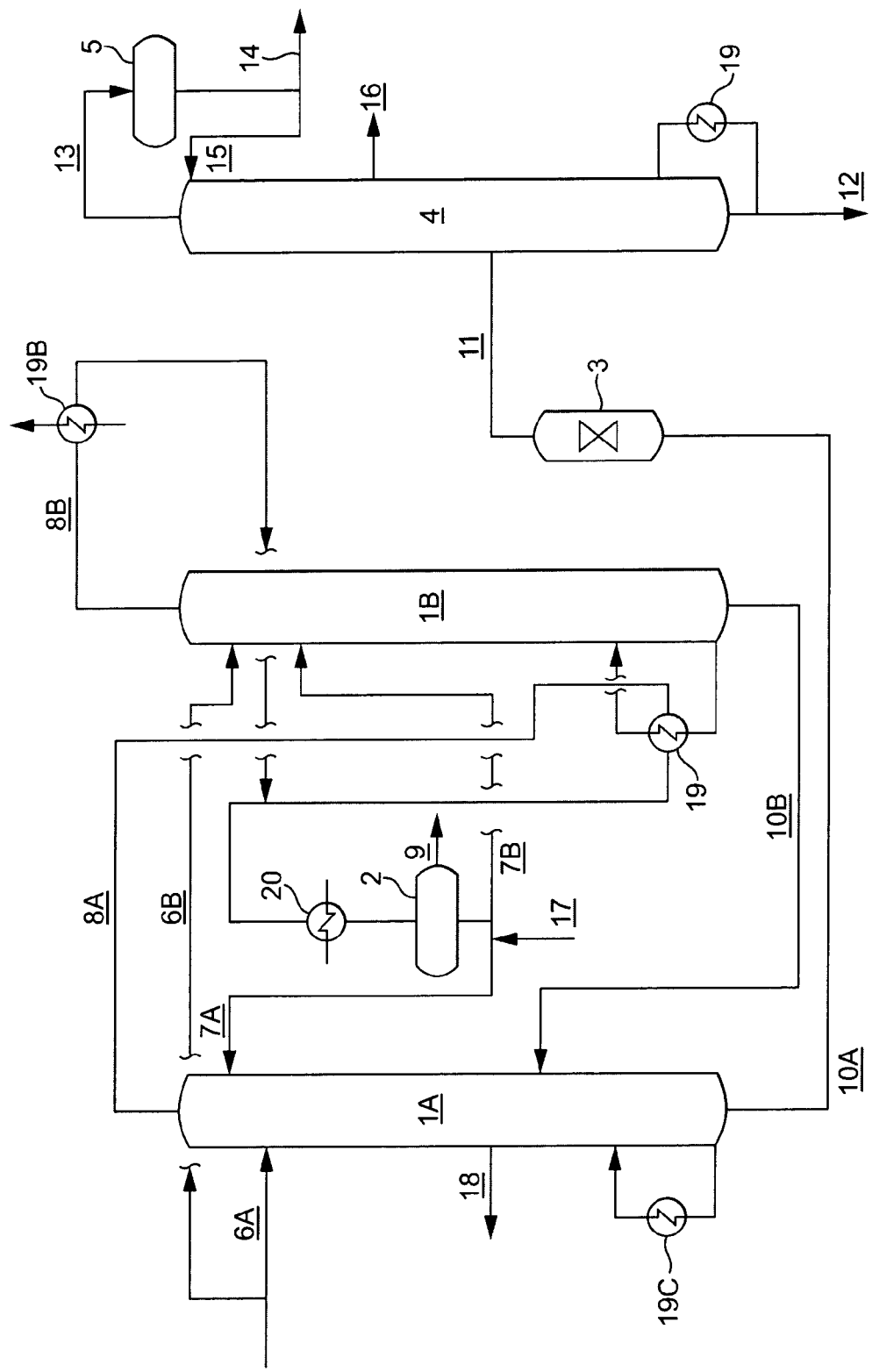

TREATMENT OF PHENOL

BACKGROUND OF THE INVENTION

1. Field of the Invention

The present invention concerns a process for the removal of by-products from a phenolic mixture.

2. Description of Related Art

Phenol is commonly manufactured through a cumene procedure, wherein cumene is oxidized to cumene hydroperoxide (CHP) and the resulting oxidation product mixture is concentrated and subjected to a cleavage reaction. Subsequently, the cleavage product mixture is conducted to a distillation section, wherein the main products of the cleavage reaction, i.e. phenol and acetone, are first separated and then purified through a series of distillation steps or other purification steps. The crude phenol resulting from the separation of phenol and acetone contains several by-products, which are difficult or almost impossible to remove with conventional distillation. These by-products are for example α-methyl styrene (AMS), acetophenone residues, mesityl oxide and 2-methylbenzofurane.

Some of the mentioned by-products are insoluble in water and when mixed with phenol they may form heterogenic azeotropes. The boiling points of these azeotropes are generally in the same region as the boiling point of phenol, whereby their substantially complete removal with distillation is impossible.

Common phenol purification methods include hydroextraction (EP 0,505,146), extractive distillation (EP 0,571,042) and resin treatment (U.S. Pat. No. 5,414,154).

One more effective phenol purification procedure is a combination of a distillation and a resin treatment. A procedure of this type is presented in EP publications 1,395,540 and 1,727,779, wherein the phenol mixture to be purified is subjected to a resin treatment with an acidic resin, whereafter the product mixture is distilled to separate phenol from higher boiling compounds.

Since the resin treatment involves trapping by-products in a resin, which by-products deactivate the resin, the resin lifetime depends on the amount of by-products in the feed of the resin bed reactor. If, for example, the phenol to be purified has been manufactured through the above mentioned cumene oxidation and cleavage procedure, it may contain several different by-products, such as α-methyl styrene (AMS), hydroxyacetone, acetophenone residues, mesityl oxide, 2-methylbenzofurane, t-butyl benzene, cyclohexanol, phenyl dimethyl carbinol and other organic components, e.g. ketones and dimers. Since a large amount of by-products in the mixture results in a short lifetime for the resin and since a change of resin results in a stoppage of the phenol production, it would be advantageous to minimize the amount of by-products in the feed of the resin bed reactor.

One of the mentioned by-products is AMS, which is a water-insoluble compound formed from the oxidation by-product dimethyl phenyl carbinol (DMPC) by dehydration during the acid catalyzed cleavage of the main oxidation product CHP. AMS is a very reactive molecule, making it extremely harmful for a catalyst of the resin type, such as an ion exchange resin, since it causes catalyst deactivation.

SUMMARY OF THE INVENTION

It is an aim of the present invention to provide an efficient phenol purification process.

Particularly, it is an aim of the present invention to provide a purification process containing a step of resin treatment with a feed quality that is improved compared to the feed quality of the prior art. Moreover, this should be achieved whilst maximising the phenol output.

These and other objects, together with the advantages thereof over known methods, are achieved by the present invention, as hereinafter described and claimed.

The present invention concerns a process for the removal of by-products from a phenolic mixture, which process comprises a first extractive distillation to give an initial phenolic mixture. Contacting the initial phenolic mixture containing phenol and one or more by-products, such as α-methyl styrene (AMS), acetophenone residues, hydroxyacetone, mesityl oxide, 2-methylbenzofurane, t-butyl benzene, cyclohexanol, phenyl dimethyl carbinol and other organic components, with a catalyst to produce a first purified phenol product mixture, and distilling the first purified phenol product mixture to produce a second purified phenol product mixture.

The present invention also concerns an apparatus for purifying a phenolic mixture.

Viewed from one aspect the invention provides a process for the removal of by-products from a phenolic mixture, which process comprises the following steps:
  subjecting a phenolic mixture to extractive distillation to produce an initial phenolic mixture,
  contacting said initial phenolic mixture containing phenol and one or more by-products with a catalyst to produce a first purified phenol product mixture, and
  distilling the first purified phenol product mixture to produce a second purified phenol product mixture;
  wherein the extractive distillation is preferably carried out in two columns, a higher pressure column and a lower pressure column.

Viewed from another aspect the invention provides an apparatus for the removal of by-products from a phenolic mixture, comprising
  two columns for extractive distillation (1A) and (1B) positioned upstream from the resin bed reactor (3), which column (1A) is in fluid communication with the reactor (3), in which in columns (1A) and (1B) the phenolic mixture may be subjected to extractive distillation;
  wherein column (1A) contains inlets (6A) for the column feed, a water-phenol azeotrope inlet (7A), a base product outlet (10A), an overhead outlet (8A) and an intermediate outlet (18);
  a resin bed reactor (3) containing a catalyst, which may be contacted with a phenolic mixture containing phenol and by-products; and
  a distillation column (4) positioned downstream from the resin bed reactor (3) in fluid communication with the reactor (3), in which distillation column (4) the phenolic mixture may be distilled;

Considerable advantages are obtained by means of the invention. Thus, the present invention provides a phenol purification process, including a step of catalyst treatment, wherein the feed of a resin bed reactor is purified by fractional distillation and extractive distillation, where, among others, water-insoluble by-products may be removed from the mixture to be purified, whereby the catalyst lifetime is increased through the decrease in the amount of fouling. This further results in an increased purity of the phenol product.

Next, the invention will be described more closely with reference to the attached drawing and the following detailed description.

BRIEF DESCRIPTION OF THE DRAWING

FIG. 1 is a schematic representation of a preferred embodiment of the present invention.

DETAILED DESCRIPTION OF THE PREFERRED EMBODIMENTS OF THE INVENTION

The present invention concerns a process for the removal of by-products from a phenolic mixture, which process comprises contacting an initial phenolic mixture containing phenol and one or more by-products of phenol production with a catalyst to produce a first purified phenol product mixture, and distilling the first purified phenol product mixture to produce a second purified phenol product mixture. The mentioned by-products are typically carbonyls or aromatic or alicyclic compounds. Examples include α-methyl styrene (AMS), cumene, hydroxyacetone, acetophenone residues, mesityl oxide, 2-methylbenzofurane, t-butyl benzene, cyclohexanol, phenyl dimethyl carbinol and other organic components.

Particularly, the present invention concerns a process for the removal of by-products from a phenolic mixture, the process comprising subjecting the phenolic mixture to extractive distillation to produce an initial purified phenolic mixture, which is to be contacted with the catalyst.

The term "distillation" is intended to mean a method of separating chemical components based on differences in their volatilities. The mixture conducted to the distillation column, wherein the distillation takes place, is separated into at least a distillate or an overhead fraction containing "light" components, i.e., components that vaporize under the conditions prevailing in the column, and an unevaporated fraction, or a base product, containing "heavy" components, i.e., components that remain in liquid form under the conditions prevailing in the distillation column.

"Extractive distillation" is a distillation of a mixture in the presence of a miscible, relatively nonvolatile solvent. The solvent is chosen to interact with the components of the mixture, thereby altering their relative volatilities. Preferably the solvent is water.

The apparatus of the present invention for removing by-products from a phenolic mixture contains the following parts (FIG. 1):

| | |
|---|---|
| 1A/1B | columns for extractive distillation |
| 2 | extractive distillation overhead drum |
| 3 | resin bed reactor |
| 4 | phenol purification column |
| 5 | phenol purification overhead drum |

According to a preferred embodiment of the present invention, the apparatus further contains the following parts (FIG. 1):

| | |
|---|---|
| 6A/6B | extractive distillation feed inlet |
| 7A/7B | extractive reflux inlet |
| 8A/8B | extractive overhead outlet |
| 9 | extractive distillation by-product outlet |
| 10A | initial purified mixture feed line |
| 10B | Low Pressure Column Bottom Outlet |
| 11 | first purified product feed line |
| 12 | phenol purification base product outlet |
| 13 | phenol purification distillate outlet |
| 14 | phenol purification by-product removal line |

-continued

| | |
|---|---|
| 15 | phenolic reflux inlet |
| 16 | second purified product outlet |
| 17 | water make-up inlet |
| 18 | extractive intermediate outlet |
| 19 | Reboiler |
| 20 | Optional Condenser |

The apparatus contains at least one resin bed reactor 3 containing a catalyst, which may be contacted with a phenolic mixture. At least one distillation column 4, with an overhead drum 5, is positioned downstream from the resin bed reactor 3 in fluid communication with the reactor 3, in which distillation column 4 the mixture may be distilled. At least two columns for extractive distillation 1A/1B, with an overhead drum 2, are positioned upstream from the resin bed reactor 3, which column 1A is in fluid communication with the reactor 3, and in which column 1A and 1B the mixture may be subjected to extractive distillation.

Column 1A is the higher pressure column and column 1B is the lower pressure column. It is essential therefore that the pressure in higher pressure column is greater than in the lower pressure column, e.g. at least 0.5 barg, greater. The feed is divided and enters the columns via 6A and 6B. The bottoms stream from 1A (which can be at a temperature as high as 220° C.), is removed and transferred to the catalyst bed as described herein. Overhead stream 8A is connected to reboiler 19 of column 1B. The overhead condensate from reboiler 19 goes to overhead drum 2. The heat of condensation of overhead stream 8A is used to heat reboiler 19. A fraction from the bottom of column 1B is thus reheated through reboiler 19. The overhead stream of column 1B is condensed and returned to overhead drum 2. The heat of the overhead can be used to hat reboiler 19b. A condenser 20 may be used prior to overhead drum 2 to control the temperature of the overhead streams. This is not essential.

The lower water/phenol phase from the overhead drum is divided and returned to columns 1A and 1B via lines 7A and 7B. In drum 2, the upper phase is removed via line 9.

Column 1B is operated at lower pressure than column 1A. The overhead from column 1B is recycled back to condensate drum 2. The temperature of the overhead stream is hot enough that it can be used to power reboilers in other parts of the phenol production process. The bottoms fraction 10B of column 1B is recycled back to column 1A.

Column 1A is preferably provided with side reboilers which can be operated with low pressure steam.

According to an embodiment of the present invention, the columns for extractive distillation are hydroextraction columns and contain inlets 6A/6B for a hydroextraction feed, i.e. a phenolic mixture, a reflux inlet 7A, at which also a water inlet 17 is positioned, a base product outlet connected to a feed line 10A for the initial phenolic mixture, an overhead outlet 8A in fluid communication with the extractive distillation overhead drum 2, with a by-product outlet 9 mainly for hydrocarbons, and an intermediate outlet 18 for removing at least a portion of the by-products. The inlet 6A/6B for the hydroextraction feed is preferably connected to the distillation section of a phenol purification zone.

According to another embodiment of the present invention, the feed line 10A for the initial phenolic mixture is connected to a resin feed inlet of the resin bed reactor 3. According to this embodiment an outlet of the resin bed reactor 3 is connected to a first purified product feed line 11, also connected to a feed inlet of the at least one phenol purification column 4.

According to a further embodiment of the present invention, the purification column 4 further contains a base product outlet 12, a distillate outlet 13, which is in fluid communication with the distillation overhead drum 5, which, in turn, is connected to a by-product removal line 14, a reflux inlet 15, also connected to the by-product removal line 14 and in fluid communication with the overhead drum 5, and an outlet 16 for the second purified product.

The purification process and the apparatus of the present invention may be used for removing by-products from any mixture containing at least two organic compounds. Preferably, the apparatus is arranged in the distillation section of a phenol production process. The phenol production process typically comprises process steps, wherein phenol and acetone are produced through the oxidation of cumene to cumene hydroperoxide (CHP) and, subsequently, wherein the CHP is concentrated and cleaved into phenol, acetone and other cleavage products, such as water, cumene, AMS, hydroxyacetone, mesityl oxide, acetophenone, carbinol and heavy hydrocarbons, whereafter the main products phenol and acetone are washed and desalted, and finally separated and purified.

In the context of the present invention, the term "phenolic mixture" refers to any product mixture or feed containing phenol as well as one or more by-products. The term "catalyst treatment feed" or "resin bed reactor feed" refers to a phenolic mixture that is being conducted to a resin bed reactor 3. Likewise, the terms "distillation feed" and "extraction feed" or "hydroextraction feed" refer to a phenolic mixture that is being conducted to a distillation column 4 and a column for extractive distillation 1A/B, respectively. Thus, the "catalyst treatment feed" or the "resin bed reactor feed" also refers to the initial phenolic mixture of the invention, whereas the "distillation feed" also refers to the first purified phenol product mixture.

According to the present invention, a phenolic mixture is conducted to a column for extractive distillation, optionally through one or more further distillation columns, in which columns by-products may be separated from the phenolic mixture through fractional distillation, extractive distillation, resin purification or any other phenol purification procedure.

According to an embodiment of the present invention, by-products such as 2-methylbenzo-furane, mesityloxide, benzaldehyde and AMS are separated from the phenolic mixture in the extractive distillation columns. In these columns, the phenolic mixture is subjected to extractive distillation, whereby an initial portion of by-products are separated from the phenolic mixture, preferably into an overhead fraction and an intermediate fraction, and an initial purified phenol product mixture is formed as the base product. Thus, the base product formed during the extractive distillation contains most of the phenol of the feed conducted to the columns 1A/1B, and is thus conducted further to the subsequent purification steps.

During the extractive distillation, a portion of more than 80%, preferably more than 98%, and most preferably more than 99.5%, of the by-products are removed from the phenolic mixture. For example, the concentration of 2-methylbenzofuran may be decreased to a level of preferably less than 15 wppm, more preferably less than 7 wppm and most preferably less than 2 wppm.

According to a preferred embodiment of the invention, the extractive distillation is carried out as a hydroextraction, whereby by-products are removed from the phenolic mixture in a hydroextraction through water elution with added fresh or recycled water or a mixture of these. The water concentration of the base product, during the hydroextraction, is maintained at only about 50-500 ppm, preferably about 300 ppm.

The optionally added fresh water is water essentially free from hydrocarbons. Preferably, this fresh water consists of condensed water.

The overhead fraction formed during the hydroextraction is condensed in an overhead drum 2, which is in fluid communication with the hydroextraction column 1A and 1B, whereby two phases separate, the phases being a lower phase and an upper phase. The lower phase, which contains phenolic water, is recycled back to the columns 1A/B as reflux, whereas the upper phase, containing hydrocarbon by-products, is removed. The ratio of recycled phenolic water to the phenolic feed of the columns 1 is about 0.5:1-3.0:1. This ratio is preferably constant. Higher reflux rates are preferred.

The overhead drum 2 contains two zones, a water zone and a hydrocarbon zone. The drum 2 is important for the final phenol product quality. By-products, which are conducted to the overhead drum 2 from the columns 1, are separated from water in the drum 2 and are subsequently conducted to the hydrocarbon side, from where they can be removed.

According to an embodiment of the invention, cumene or AMS is added, e.g. to the overhead drum 2 to improve removal of impurities from the water phase.

Thus, viewed from another aspect the invention provides a process for the removal of by-products from a phenolic mixture, as hereinbefore described in which the phenolic mixture is subjected to a hydroextractive distillation to produce a base initial phenolic mixture and an overhead stream;
    allowing said overhead stream to separate into a lower and upper phases and recycling the lower phase back into the hydroextrative distillation.

Maintaining a low phenol concentration in the hydroextraction overhead fraction is important, because this improves the separation of hydrocarbons from the water. The distillation is conducted so that the overhead fraction contains essentially only phenol/water azeotropes. Good phase separation is achieved by maintaining the temperature of the overhead fraction at a sufficiently high level, which generally is at least 60° C., preferably about 70° C., most preferably about 85° C.

The aqueous phase of the overhead fraction, containing the phenolic water, may be used over and over again, because the by-products are not concentrated in the reflux water. This is a significant advantage in the purification process of the invention. Pure water is still required to be fed to the reflux of the column 1 to replace shortage of water due to its removal with the hydrocarbon phase and the base product among others.

A particular advantage of placing a hydroextraction column upstream from a resin bed reactor 3, when purifying a phenolic mixture, is that water-insoluble by-products, such as AMS, which as a very reactive molecule is capable of deactivating the catalyst of the resin bed reactor 3, may be removed from the phenolic mixture before causing any deactivation. Other by-products removed from the phenolic mixture in the hydroextraction columns are components, such as t-butylbenzene, mesityl oxide and 2-methylbenzofuran, at least a portion of which are separated from the phenolic mixture as an organic fraction.

In the hydroextraction distillation some by-products with high boiling points or water-soluble by-products may remain in the water phase, further containing phenolic water, and they could therefore concentrate in the hydroextraction column 1, therefore causing corrosion. Such by-products are for example diacetonealcohol, some $C_5$- and $C_6$-ketoalcohol residues and different water-soluble organic acids. To solve this potential problem, these by-products are removed from the column 1A through an intermediate outlet 18 positioned at the side of the column 1A. This purge stream is small and almost pure phenol The phenolic mixture being conducted from the base of the column 1A for extractive distillation to the resin bed reactor 3, i.e., the initial phenolic mixture, still contains some by-products, which are harmful in the end product, causing for example color formation in the purified phenol. These by-products may, however, be removed through treatment with a catalyst in the resin bed reactor 3. This is achieved by contacting the initial phenolic mixture, being conducted to the resin bed reactor 3, with a catalyst, whereby a first portion of the by-products are separated from the phenolic mixture and a first purified phenol product mixture is formed. This treatment causes light by-products to react into heavier hydrocarbons that can be separated from the phenol in a final distillation step.

The feed for the catalyst treatment may be conducted through a series of heat exchangers, in which it is cooled down. After being cooled, the feed is conducted to the resin bed reactor 3, where the catalyst treatment takes place preferably at a temperature of about 70-110° C.

According to a preferred embodiment of the invention, the catalyst in the resin bed reactor 3 is a resin, preferably an ion exchange resin, most preferably a strong acid polymeric resin, such as an Amberlyst™ resin. Ion exchange resins are available in two types, macroreticular and gel types. Examples of commercially available, suitable resins include, but are not limited to, Amberlyst™ A-15, Amberlyst™ A-36, Purolite™ CT-251 and Lewitat K2431. The catalyst may also be a solid superacid catalyst or similar. Preferably, the resin is based on a sulfonated divinylbenzene styrene copolymer.

The catalyst causes at least a portion of the by-products in the catalyst treatment feed to react and form heavier compounds, the portion of hydroxyacetone, mesityloxide, AMS, 2-methylbenzofuran preferably being 80-99.5% of the by-products remaining in the feed, more preferably 90-99.8%, most preferably 95-99.8%. Due to the effect of the catalyst, the hydroxyacetone concentration in the phenolic mixture conducted through the resin bed reactor 3 decreases to a level below 1 ppm and the concentration of carbonyl by-products decreases to a level below 15 wppm. The use of the catalyst causes some by-products to react with phenol and therefore to release water. This causes the water concentration to increase downstream from the resin bed reactor 3.

According to the preferred embodiment of the invention, the hydroxyacetone concentration in the catalyst treatment feed is preferably less than 50 wppm, more preferably less than 20 wppm. Hydroxyacetone reacts into 2-MBF in the resin bed and, therefore, it is important to have a low hydroxyacetone concentration in the feed. It is also important that the extractive distillation, which is positioned upstream from the fractional distillation, separates the hydroxyacetone from the product fraction, since the fractional distillation is not efficient for this separation.

According to the preferred embodiment of the invention AMS concentration in the resin bed reactor feed is preferably less than 100 wppm, more preferably less than 10 ppm. As a reactive component AMS will deactivate catalyst by forming heavier polymers and thus shorten catalyst life.

The resin bed reactor 3 is operated at as low temperatures as possible during the whole operating period. Generally, the temperature is 50-130° C., preferably 70-110° C. A decrease in the activity of the catalyst causes a need to increase the temperature. While this higher temperature does restore the activity of the catalyst, it also accelerates the loss of catalyst. The maximum temperature for the catalyst and the residence time of the phenolic mixture in the resin bed reactor 3 depend on factors such as the type of catalyst and the size of the reactor 3.

From the resin bed reactor 3, the phenolic mixture (i.e. the first purified phenol product mixture, at this point) is conducted further to the phenol distillation column 4, wherein it is distilled in order to separate a second portion of the by-products from the phenol and to produce a second purified phenol product mixture. Thus, a base product, an intermediate fraction and a distillate are formed, whereby the base product contains most of the high boiling by-products, the distillate contains most of the low boiling by-products and of the water, and the intermediate fraction contains most of the phenol. High boiling by-products, such as the ones formed during the catalyst treatment, e.g., ortho- and paracumyl phenols and acetophenone, are removed from the mixture as the base product, whereas water is removed, together with any low boiling compounds, as the distillate. The purified phenol product, i.e., the second purified phenol product mixture, is removed as the intermediate fraction.

The final step of phenol purification, i.e., the distillation, occurs below atmospheric pressure, preferably at about 40-80 kPa, more preferably at about 50 kPa, so that thermal decomposition of the by-products is minimized. Decomposition would result in low boiling compounds that would be difficult to separate from the phenol product and would, therefore, cause fouling of the product.

The phenol distillation column 4 is divided into three zones, a stripping zone with a purpose to concentrate high boiling by-products to the base of the column, an intermediate zone used for the separation of high boiling by-products from phenol, and a pasteurization zone with the purpose to separate water and possible lighter hydrocarbons from phenol. Column plates are preferably used to facilitate the separation.

The purified phenol product is removed through an outlet 16 in the pasteurization zone.

The pasteurization zone functions with recycle except for a further flow, removed from the distillate through a removal line 14 positioned downstream from the overhead drum 5. The purpose of this further flow is to remove at least a first portion of the water and possible lighter hydrocarbons from the distillate recycle of the distillation column 4, whereafter the second recycled portion is conducted through the phenolic reflux inlet 15 back into the column 4.

The phenol product is not completely dry, because balance is predominant with water/phenol mixtures. The concentration of by-products in the base of the column 4 is not allowed to increase to a very high level, because thermal decomposition is to be avoided. A maximum level is about 0.1-5 weight-%.

After purification, the temperature of the purified phenol product (i.e. the second purified phenol product mixture) is lowered to about 60° C. In this purified product, the concentration of each of the by-products mesityloxide, AMS, 2-methylbenzofurane and hydroxyacetone has decreased to a level of less than 5 wppm, preferably less than 3 wppm and most preferably less than 1 wppm.

According to a particularly preferred embodiment of the present invention, a washed and desalted cleavage product mixture of a phenol production process is fractioned in two steps to produce the extraction feed. The washed cleavage product is at first fractionated into a mixture comprising mainly acetone, cumene, AMS, and water and into a mixture comprising mainly phenol, phenol impurities and heavy ends. The phenol stream is further fractioned into a heavy end fraction and into an extraction feed fraction.

After this mentioned fractional distillation, the phenol concentration of the extraction feed fraction is about 95.0-99.7, preferably 97.0-99.6, and more preferably 98.5-99.6 w-%.

Further, the hydroxyacetone concentration is less than 50 wppm and more preferably less than 20 wppm, whereas the 2-methylbenzofurane concentration is about 0.01-0.1 w-%.

Viewed from another aspect therefore the invention provides a process as hereinbefore defined in which said extraction feed is obtained by distillation of a washed and desalted cleavage product mixture.

The extractive distillation is performed in two columns. The first column functions with an operating pressure that is higher than the pressure in the second column. This provides a possibility for heat integration in the extractive distillation so that the high-pressure column reboils the low pressure column. The feed to the extractive distillation may be divided into both columns. The overhead systems may be combined and collected into one condensate drum and the water phase may be recycled to both columns as reflux. This arrangement allows for a 20-50% decrease in utility consumption. The operating pressure of the high-pressure column may be 0.5-4 barg and the operating pressure of the low pressure column may be 0.05-1 barg. It is essential however that the values are chosen so that column 1A operates at higher pressure. The difference in pressure is preferably at least 0.25 barg, preferably at least 0.5 barg. The concentration of water in the bottoms fraction in the low-pressure column is so high that the temperature in the column allows for the use of the high pressure column overhead for reboiling. The bottoms fraction of the low-pressure column is returned to the bottom section of the high pressure column for removal of water.

Thus viewed from another aspect the invention provides a process removal of by-products from a phenolic mixture, which process comprises the following steps:
subjecting a phenolic mixture to extractive distillation to produce an initial phenolic mixture,
contacting said initial phenolic mixture containing phenol and one or more by-products with a catalyst to produce a first purified phenol product mixture, and
distilling the first purified phenol product mixture to produce a second purified phenol product mixture; wherein
the extractive distillation is effected in two columns, a higher pressure column and a lower pressure column in which the initial phenolic mixture is extracted as the bottom stream of the higher pressure column
columns 1A/1B are provided with an overhead drum 2,
the feed is divided and enters both columns (e.g. via 6A and 6B);
the bottoms stream from column 1A, is removed and transferred to the catalyst bed
overhead stream 8A is connected to a reboiler 19 of column 1B;
the overhead condensate from the reboiler 19 goes to overhead drum 2;
the heat of condensation of overhead stream 8A is used to heat reboiler 19;
a fraction from the bottom of column 1B is reheated through reboiler 19;
the overhead stream of column 1B is returned to overhead drum 2;
a phase separation takes place in drum 2
the lower water/phenol phase from the overhead drum is divided and returned to columns 1A and 1B (e.g. via lines 7A and 7B);
the upper phase from drum 2 is removed (e.g. via line 9);
the overhead from column 1B is recycled back to drum 2;
the bottoms fraction 10B of column 1B is recycled back to column 1A.
water is added to the lower water/phenol phase recycle (e.g. via an inlet 17)

By operating in this fashion, the amount of energy required to run the process of the invention is reduced. By using this set up, the primary energy used for the reboiling column 1a can be reused for reboiling of column 1b. According to the invention extration feeds can be divided in ratios from 1:4 to 4:1 (6a/6b) to columns 1a/1b. This provides wide range for optimization of capital investment like heat exchanger surface and energy consumption. Moreover, the process of the invention can be run at a higher reflex rate.

It is further preferred if both overhead streams which may contain uncondensed phenolic water are connected and condensed and cooled in the same condenser before entering overhead drum 2. It is preferred if the aqueous phase formed in the condenser is recycled to both higher pressure and lower pressure columns.

EXAMPLE

The Example illustrates the importance of the extractive distillation in providing a low impurity feed. Two phenol streams were passed through a bed of acidic resin (Amberlyst 16) using a residence time of 60 minutes. Feed 1 was a typical feed for a resin bed reactor. Feed 2 was a typical feed for extractive distillation. The concentrations of AMS, mesityloxide, and 2-methylbenzofuran were about 1000 times higher or more in the extractive distillation feed (Feed 2) compared to the feed to the resin bed (Feed 1). The hydroxyacetone concentration was 17 wppm in Feed 1 and 7 wppm in Feed 2.

The formation of heavy components in the resin bed includes the formation of some polymers. This causes the resin to eventually become fouled with polymer. A larger amount of reactive components in the feed also results in the formation of a larger amount of polymer. The difference in the concentrations of reactive components has a significant effect on the catalyst life.

As can be seen from Table 1, the rate of AMS conversion is high and means a significant loss of AMS. Thus, by extractive distillation AMS can be recovered and hydrogenated to cumene.

The rate of hydroxyacetone conversion to 2-MBF is not significant when the hydroxyacetone concentration is below 20 wppm. The results indicated in Table 1 also show that, when the 2-MBF (2-methyl benzofuran) concentration is 760 wppm or more, some of the 2-MBF is not converted. In this case, the 2-MBF concentration will also be high in the final product because the final purification column is not efficient for removing 2-MBF.

These results (Table 1) also show that the performance of the upstream extractive distillation and the resin purification is essential for the phenol product quality.

TABLE 1

|  | Resin treatment A-16 | | Resin treatment A-16 | |
| --- | --- | --- | --- | --- |
| temperature, ° C. | 90 | | 100 | |
| residence time, min | 60 | | 60 | |
| Components | Feed 1 (resin bed feed) wppm | Treated phenol stream wppm | Feed 2 (Extractive distillation feed) wppm | Treated phenol stream wppm |
| water | 850 | 3780 | 410 | 1200 |
| carbonyls | 90 | 15 | 2010 | 295 |
| hydroxyacetone | 17 | <0.5 | 7 | <1 |
| mesityloxide | 0.7 | <0.5 | 1520 | 9 |
| AMS | 3.6 | <0.5 | 9870 | 92 |
| 3-methylcyclopetanone | 8.3 | 1.7 | 187 | 34 |

TABLE 1-continued

| | | | | |
|---|---|---|---|---|
| cyclohexanol | 3 | 0.9 | 342 | 33 |
| benzofurane | 0.2 | <0.5 | 152 | 2 |
| benzaldehyde | 1.9 | <0.5 | 45 | 5 |
| 2-MBF | 6.3 | 1.8 | 760 | 42 |

I claim:

1. A process for the removal of by-products from a phenolic mixture, which process comprises the following steps:
    subjecting a phenolic mixture to extractive distillation to produce an initial phenolic mixture containing phenol and one or more by-products,
    contacting said initial phenolic mixture containing phenol and one or more by-products with a catalyst to produce a first purified phenol product mixture, and
    distilling the first purified phenol product mixture to produce a second purified phenol product mixture;
    wherein the extractive distillation is carried out in two columns, a higher pressure column and a lower pressure column.

2. The process of claim 1, characterized in that the one or more by-products of the initial phenolic mixture are selected from the group consisting of [alpha]-methyl styrene (AMS), cumene, hydroxyacetone, acetophenone residues, mesityl oxide, 2-methylbenzofurane, t-butyl benzene, cyclohexanol, phenyl dimethyl carbinol and other organic components.

3. The process of claim 1, characterized in that the step of extractive distillation is a step of hydroextraction.

4. The process of claim 3, characterized by the addition of fresh or recycled water or a mixture of these to the step of hydroextraction to form a vapour phase and to achieve elution of by-products into said vapour phase.

5. The process of claim 4, characterized in that the fresh water is water essentially free from hydrocarbons.

6. The process of claim 1, characterized by the formation of a base product fraction and an overhead fraction during the extractive distillation, whereby the base product fraction contains most of the phenol.

7. The process of claim 6, characterized in that the base product fraction contains about 50-500 ppm of water.

8. The process of claim 6, characterized by condensing the overhead fraction formed during the extractive distillation, whereby two phases separate, the phases being a lower phase and an upper phase.

9. The process of claim 8, characterized by maintaining the temperature of the overhead fraction at above 60° C.

10. The process of claim 8, characterized in that the lower phase contains phenolic water.

11. The process of claim 10, characterized by recycling the phenolic water back to the step of extractive distillation.

12. The process of claim 11, characterized by maintaining the ratio of recycled phenolic water to the hydroextraction feed between about 0.5:1 and 3.0:1.

13. The process of claim 8, characterized in that the upper phase contains hydrocarbon by-products.

14. The process of claim 1, characterized by maintaining the catalyst temperature at about 70-110° C. during the catalyst treatment of the initial phenolic mixture.

15. The process of claim 1, characterized in that the catalyst is a resin.

16. The process of claim 1, characterized by reacting light by-products to form heavier hydrocarbons during the step of contacting the initial phenolic mixture with the catalyst.

17. The process of claim 1, characterized by forming a base product fraction, an intermediate fraction and a distillate during the distillation of the first purified phenol product mixture, whereby the base product fraction contains most of the high boiling by-products, the distillate contains most of the low boiling by-products and of the water, and the intermediate fraction contains most of the phenol.

18. The process of claim 17 wherein the intermediate fraction is removed as a side cut.

19. The process of claim 1, characterized by carrying out the distillation of the first purified phenol product mixture at low pressure.

20. The process of claim 1, characterized by performing the extractive distillation first at a higher pressure and then at a lower pressure, whereby:
    the higher pressure distillation overhead stream reboils the bottom of the column used for the lower pressure distillation, and
    the lower pressure distillation bottoms fraction is returned to the higher pressure distillation.

21. A process as claimed in claim 1 in which said at least two columns for extractive distillation 1A/1B are provided with an overhead drum,
    the feed is divided and enters both columns;
    the bottoms stream from column 1A, is removed and transferred to the catalyst bed;
    the overhead stream is connected to a reboiler of column 1B;
    the overhead condensate from the reboiler goes to the overhead drum;
    the heat of condensation of the overhead stream is used to heat the reboiler;
    a fraction from the bottom of column 1B is reheated through the reboiler;
    the overhead stream of column 1B is returned to the overhead drum;
    a phase separation takes place in the overhead drum;
    the lower water/phenol phase from the overhead drum is divided and returned to columns 1A and 1B;
    the upper phase from the overhead drum is removed;
    the overhead from column 1B is recycled back to the overhead drum;
    the bottoms fraction of column 1B is recycled back to column 1A;
    water is added to the lower water/phenol phase recycle.

22. The process of claim 6, characterized in that the base product fraction contains about 300 ppm of water.

23. The process of claim 8, characterized by maintaining the temperature of the overhead fraction at above 70° C.

24. The process of claim 8, characterized by maintaining the temperature of the overhead fraction at above 85° C.

25. The process of claim 1, characterized in that the catalyst is an ion exchange resin.

26. The process of claim 1, characterized in that the catalyst is a cation resin.

27. The process of claim 1, characterized by carrying out the distillation of the first purified phenol product mixture at below atmospheric pressure.

28. The process of claim 1, characterized by carrying out the distillation of the first purified phenol product mixture at about 50 kPa.

* * * * *